(12) United States Patent
Westphal

(10) Patent No.: US 9,205,163 B2
(45) Date of Patent: Dec. 8, 2015

(54) VOLATILE MATERIAL DISPENSER

(71) Applicant: S.C. Johnson & Son, Inc., Racine, WI (US)

(72) Inventor: Nathan R. Westphal, Union Grove, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 252 days.

(21) Appl. No.: 13/947,900

(22) Filed: Jul. 22, 2013

(65) Prior Publication Data

US 2014/0145005 A1 May 29, 2014

Related U.S. Application Data

(63) Continuation-in-part of application No. 13/686,657, filed on Nov. 27, 2012.

(51) Int. Cl.
*A61L 9/12* (2006.01)

(52) U.S. Cl.
CPC .............. *A61L 9/12* (2013.01); *A61L 2209/11* (2013.01); *A61L 2209/131* (2013.01); *A61L 2209/133* (2013.01); *A61L 2209/15* (2013.01)

(58) Field of Classification Search
CPC . A61L 9/12; A61L 2209/11; A61L 2209/131; A61L 2209/133
See application file for complete search history.

(56) References Cited

U.S. PATENT DOCUMENTS

| | | | |
|---|---|---|---|
| 1,732,028 A * | 10/1929 | Reiner | 239/36 |
| 2,247,600 A | 7/1941 | Brennen et al. | |
| 2,412,326 A * | 12/1946 | Dupuy | 239/51.5 |
| 2,642,310 A | 6/1953 | Meek et al. | |
| 2,657,090 A * | 10/1953 | Meek | 239/55 |
| 2,765,194 A * | 10/1956 | Theodore | 239/59 |
| 3,976,246 A | 8/1976 | Hauri et al. | |
| 3,991,915 A | 11/1976 | Kinnavy | |
| 4,040,568 A | 8/1977 | Mason, Jr. et al. | |
| 4,067,692 A | 1/1978 | Farris | |
| 4,154,398 A | 5/1979 | Gualandi | |
| 4,219,145 A | 8/1980 | Jaeschke et al. | |
| 4,248,380 A | 2/1981 | Lee et al. | |
| 4,258,004 A | 3/1981 | Valenzona et al. | |
| 4,258,874 A | 3/1981 | Webinger et al. | |
| 4,277,014 A | 7/1981 | Webinger | |
| 4,301,949 A | 11/1981 | Palson et al. | |

(Continued)

FOREIGN PATENT DOCUMENTS

| | | |
|---|---|---|
| DE | 2322717 A1 | 12/1973 |
| EP | 3003 | 7/1979 |

(Continued)

OTHER PUBLICATIONS

PCT/US2014/047028 International Search Report and Written Opinion dated Dec. 17, 2014.

(Continued)

*Primary Examiner* — Ryan Reis

(57) ABSTRACT

A dispenser includes a base for receiving a volatile material containing reservoir. A cover is attached to the base having at least one aperture and at least one series of ports. A regulating plate is operatively attached to the cover and has at least one window and at least one series of bores. Manipulation of the regulating plate allows for the registration of the bores and the ports to release a volatile material therethrough.

20 Claims, 17 Drawing Sheets

(56) References Cited

U.S. PATENT DOCUMENTS

| | | | |
|---|---|---|---|
| 4,306,679 A | 12/1981 | Dusek et al. | |
| 4,339,079 A | 7/1982 | Sato et al. | |
| 4,356,969 A | 11/1982 | Obermayer et al. | |
| 4,361,279 A | 11/1982 | Beacham | |
| 4,502,630 A | 3/1985 | Haworth et al. | |
| 4,512,933 A | 4/1985 | Harden | |
| 4,523,870 A | 6/1985 | Spector | |
| 4,572,375 A * | 2/1986 | Baer | 239/56 |
| 4,583,686 A | 4/1986 | Martens | |
| 4,630,775 A | 12/1986 | Mandon et al. | |
| 4,634,614 A | 1/1987 | Holzner | |
| 4,664,312 A * | 5/1987 | Bryson | 239/59 |
| 4,809,912 A | 3/1989 | Santini | |
| 4,849,606 A | 7/1989 | Martens, III et al. | |
| 4,865,816 A | 9/1989 | Walz et al. | |
| 4,878,615 A | 11/1989 | Losi | |
| 4,940,522 A | 7/1990 | Kagechika et al. | |
| 4,944,455 A | 7/1990 | Haust et al. | |
| 4,947,578 A | 8/1990 | Anderson et al. | |
| 4,961,532 A | 10/1990 | Tangney | |
| 4,968,456 A | 11/1990 | Muderlak et al. | |
| 5,033,674 A | 7/1991 | Smith | |
| 5,115,975 A | 5/1992 | Shilling | |
| 5,145,604 A | 9/1992 | Neumiller | |
| 5,148,984 A | 9/1992 | Bryson, Jr. et al. | |
| 5,219,121 A * | 6/1993 | Fox et al. | 239/43 |
| 5,240,487 A | 8/1993 | Kung | |
| 5,314,669 A | 5/1994 | Hamilton | |
| 5,361,522 A | 11/1994 | Green | |
| 5,388,714 A | 2/1995 | Zutler | |
| 5,478,505 A | 12/1995 | Mcelfresh et al. | |
| 5,516,504 A | 5/1996 | Tomlinson | |
| 5,527,493 A | 6/1996 | Mcelfresh et al. | |
| 5,565,148 A | 10/1996 | Pendergrass, Jr. | |
| 5,651,522 A | 7/1997 | Davis | |
| 5,695,692 A | 12/1997 | Kennedy | |
| 5,782,409 A | 7/1998 | Paul | |
| 5,868,315 A | 2/1999 | Chen | |
| 5,898,475 A | 4/1999 | Martin | |
| 5,899,382 A | 5/1999 | Hayes et al. | |
| 6,029,901 A * | 2/2000 | Toy, II | 239/55 |
| 6,080,367 A | 6/2000 | Lin | |
| 6,085,989 A | 7/2000 | Cox | |
| 6,171,608 B1 | 1/2001 | Schmitt et al. | |
| 6,241,219 B1 | 6/2001 | Logan et al. | |
| 6,244,518 B1 * | 6/2001 | Pogue | 239/36 |
| 6,254,248 B1 | 7/2001 | McAuley et al. | |
| 6,254,836 B1 | 7/2001 | Fry | |
| 6,361,788 B1 | 3/2002 | Antoni-Zimmermann et al. | |
| 6,502,762 B2 | 1/2003 | Tuttobene et al. | |
| 6,551,560 B1 | 4/2003 | Flashinski et al. | |
| 6,607,434 B2 | 8/2003 | Park | |
| 6,610,254 B1 | 8/2003 | Furner et al. | |
| 6,631,852 B1 | 10/2003 | O'Leary | |
| 6,655,604 B2 | 12/2003 | Tuttobene, Jr. | |
| 6,746,521 B2 | 6/2004 | Canfield | |
| 6,767,521 B1 | 7/2004 | Vogt et al. | |
| 6,909,840 B2 | 6/2005 | Harwig et al. | |
| 7,036,800 B2 | 5/2006 | Ellis | |
| 7,070,172 B2 | 7/2006 | Fabrega et al. | |
| 7,152,809 B2 | 12/2006 | Ketcha et al. | |
| 7,344,729 B2 | 3/2008 | Kemmis et al. | |
| 7,503,675 B2 | 3/2009 | Demarest et al. | |
| 7,544,332 B2 | 6/2009 | De Silva et al. | |
| 7,887,826 B2 | 2/2011 | Costa | |
| 7,988,073 B2 | 8/2011 | Ligny et al. | |
| 8,005,349 B2 | 8/2011 | Delorian et al. | |
| 8,047,837 B2 | 11/2011 | Furner et al. | |
| 8,048,379 B2 | 11/2011 | Sassoon | |
| 8,096,486 B2 | 1/2012 | Wang et al. | |
| 8,119,150 B2 | 2/2012 | Tamarkin et al. | |
| 8,137,715 B2 | 3/2012 | Shah et al. | |
| 2003/0038133 A1 | 2/2003 | Liu | |
| 2003/0060350 A1 | 3/2003 | Taylor et al. | |
| 2003/0068955 A1 | 4/2003 | Vick | |
| 2004/0088904 A1 | 5/2004 | Laskey et al. | |
| 2005/0042245 A1 | 2/2005 | Taranta et al. | |
| 2005/0089502 A1 | 4/2005 | Schansberg et al. | |
| 2005/0127538 A1* | 6/2005 | Fabrega et al. | 261/104 |
| 2007/0051826 A1 | 3/2007 | Schofield | |
| 2007/0057086 A1 | 3/2007 | Van Kippersluis | |
| 2008/0023568 A1 | 1/2008 | Weggelaar | |
| 2008/0095522 A1 | 4/2008 | Deflorian et al. | |
| 2008/0175913 A1 | 7/2008 | Zhang et al. | |
| 2008/0193640 A1 | 8/2008 | Zhang et al. | |
| 2008/0257978 A1 | 10/2008 | Marth et al. | |
| 2008/0277415 A1 | 11/2008 | Pirrie et al. | |
| 2009/0010813 A1 | 1/2009 | Wang et al. | |
| 2009/0118367 A1 | 5/2009 | Steward et al. | |
| 2009/0163582 A1 | 6/2009 | Wang et al. | |
| 2009/0182040 A1 | 7/2009 | Heger et al. | |
| 2009/0302128 A1 | 12/2009 | Zobele | |
| 2009/0311195 A1 | 12/2009 | Clark et al. | |
| 2010/0056422 A1 | 3/2010 | Lammert et al. | |
| 2010/0093531 A1 | 4/2010 | Habicher et al. | |
| 2010/0178042 A1 | 7/2010 | Neumann et al. | |
| 2010/0179099 A1 | 7/2010 | Laso et al. | |
| 2010/0187327 A1 | 7/2010 | Irvin | |
| 2010/0234457 A1 | 9/2010 | Taranta et al. | |
| 2010/0292323 A1 | 11/2010 | Fujii et al. | |
| 2011/0010817 A1 | 1/2011 | Theberge et al. | |
| 2011/0114663 A1 | 5/2011 | Brown et al. | |
| 2011/0117156 A1 | 5/2011 | Lin et al. | |
| 2011/0180621 A1 | 7/2011 | Gruenbacher | |
| 2011/0305644 A1 | 12/2011 | Vijay et al. | |
| 2012/0123038 A1 | 6/2012 | Wilert | |

FOREIGN PATENT DOCUMENTS

| | | |
|---|---|---|
| EP | 13195453 | 6/2003 |
| EP | 1479400 A1 | 11/2004 |
| EP | 1698355 | 6/2006 |
| EP | 2055322 | 5/2009 |
| EP | 2055322 | 6/2009 |
| GB | 1514712 | 6/1978 |
| GB | 2380940 | 4/2003 |
| GB | 2407770 | 5/2005 |
| GB | 2407771 | 5/2005 |
| WO | 9102549 A1 | 3/1991 |
| WO | 0024434 | 5/2000 |
| WO | 0220172 | 3/2002 |
| WO | 03105652 | 2/2003 |
| WO | 2005044001 | 5/2005 |
| WO | 2005056063 | 6/2005 |
| WO | 2006004899 | 1/2006 |
| WO | 2006061803 | 6/2006 |
| WO | 2006128316 | 12/2006 |
| WO | 2007110086 | 4/2007 |
| WO | 2008022477 | 11/2008 |
| WO | 2011030122 | 3/2011 |
| WO | WO 2011/072209 A1 | 6/2011 |
| WO | 2011140917 | 11/2011 |
| WO | 2012009386 | 1/2012 |
| WO | 2013012442 | 1/2013 |
| WO | 2014014920 | 1/2014 |
| WO | WO 2014/085385 A1 | 6/2014 |

OTHER PUBLICATIONS

PCT/US2013/071865 International Search Report and Written Opinion dated Apr. 1, 2014, 18 pages.

* cited by examiner

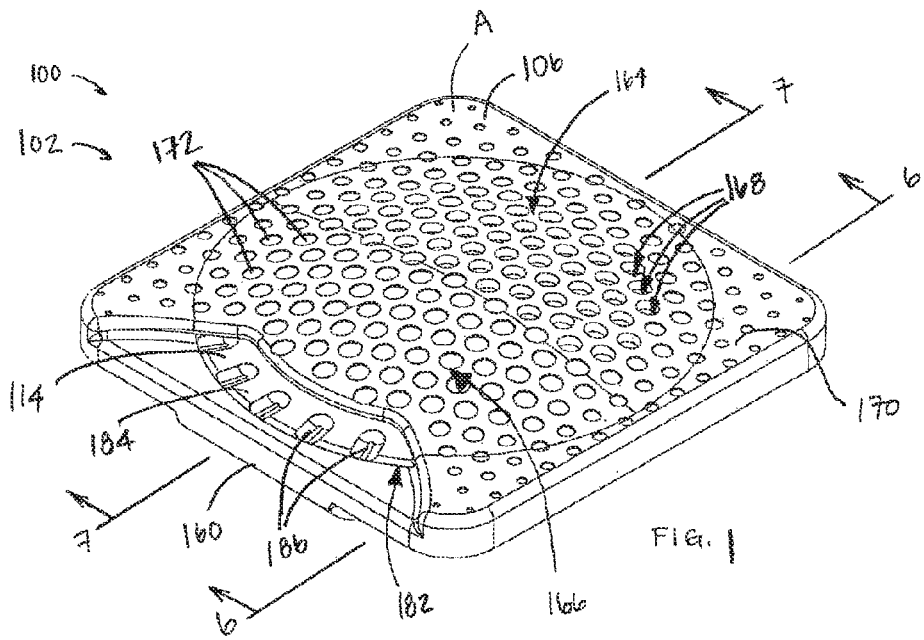
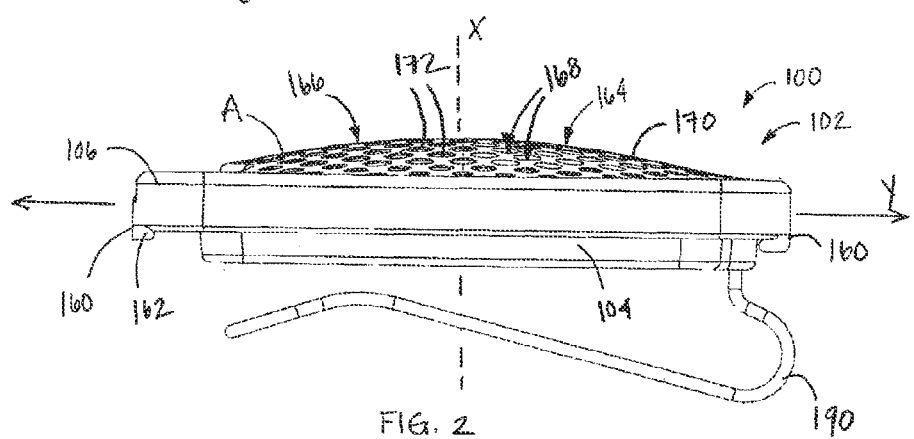

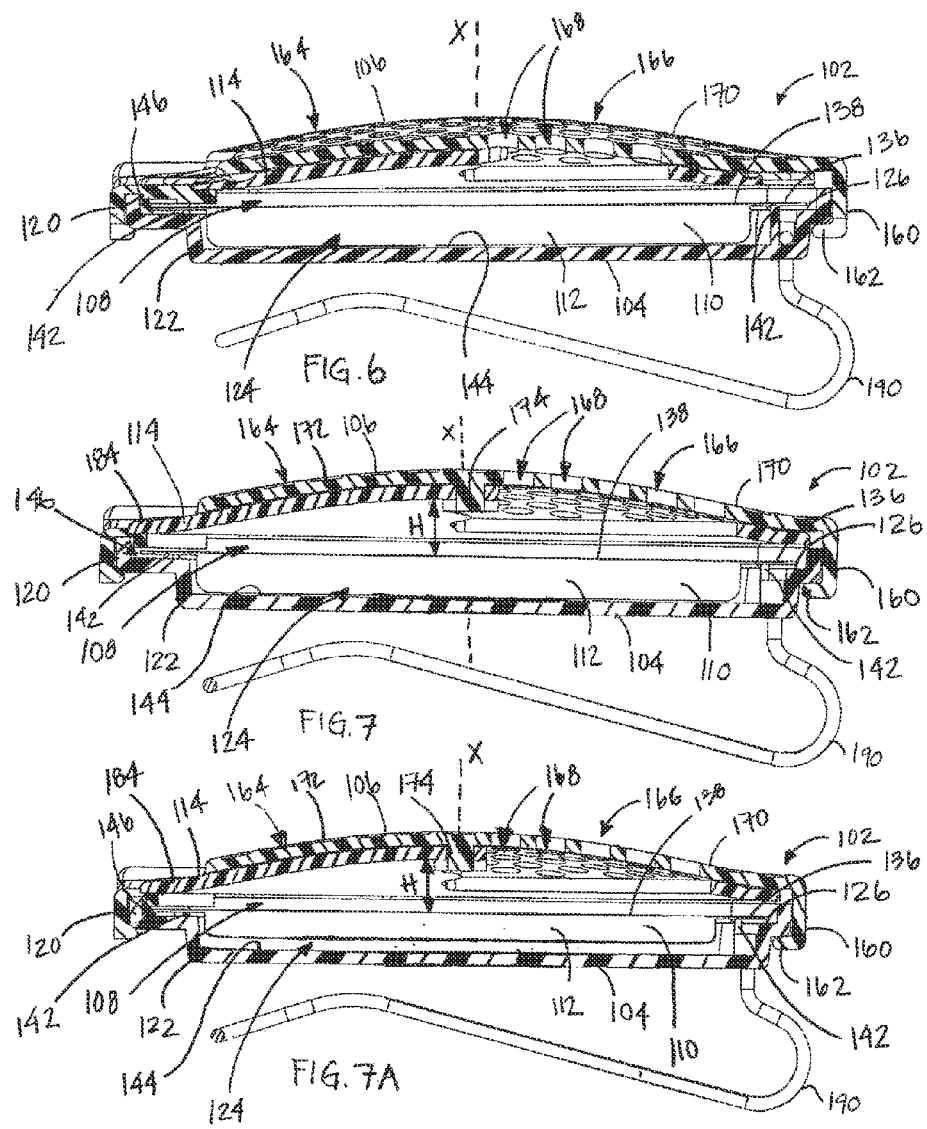

VOLATILE MATERIAL DISPENSER

CROSS REFERENCE TO RELATED APPLICATIONS

This application is a continuation-in-part of U.S. application Ser. No. 13/686,657, filed on Nov. 27, 2012.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to a volatile material dispensing system and, more specifically, to a dispenser capable of controlling the dispensing of a volatile material from a cartridge.

2. Description of the Background of the Invention

Adjustable passive dispensers are popular worldwide and, as such, consumers' demands as to the capabilities and aesthetics of such dispensers are diverse. It is therefore desirable to create a dispensing system that can easily and inexpensively be adapted to conform to local market demands and user preferences. For example, common passive dispensers utilize a volatile material refill cartridge disposed therein, however, various localities use different sized refill cartridges. It would be beneficial to manufacturers to manufacture a single dispenser that can be sold in various markets regardless of the size of the refill cartridges sold in that market. It is also beneficial to consumers to not have to worry about inserting the properly sized refill cartridge within the appropriate dispenser. Thus, there is a need for a dispenser that can receive various sized refill cartridges without compromising the performance of the dispenser.

In addition to the above-noted technical capabilities, the aesthetic appearance and size of such dispensers is also an important issue, especially with dispensers that are used and displayed in a user's car or home. Dispensers that are used in an automobile are often attached to a visor or some other visible location, in which the design of the dispenser may be readily observed. Larger, bulkier dispensers are less aesthetically pleasing and take up more visual space in the vehicle. Thus, it is important to minimize the visual weight of the dispenser. Further, while prior art dispensers are designed with current market preferences in mind, the appearance of these dispensers is not easily and inexpensively modifiable, such that manufacturers and consumers can change the appearance of the dispenser to keep up with current market trends and evolving preferences. Rather, manufacturers have to currently redesign and manufacture new dispensers to keep up with the changing market and consumers must buy a completely new dispenser in response to their changing preferences.

Therefore, there exists a need for a dispenser that is adaptable to different market specifications, both technically and aesthetically, while still providing users with an easy to use adjustable passive dispenser.

SUMMARY OF THE INVENTION

In one aspect, a dispenser includes a base adapted to receive a volatile material containing reservoir therein. A cover is attached to the base having at least one aperture and at least one series of ports. A regulating plate is operatively attached to the cover and has at least one window and at least one series of bores. Manipulation of the regulating plate allows for the registration of the bores and the ports to release a volatile material therethrough.

In another aspect, a dispenser includes a base adapted to receive a volatile material containing reservoir therein. A cover is attached to the base having at least one aperture. A regulating plate is operatively attached to the cover and has at least one window and a series of bores. The series of bores includes at least two bores, each of which is provided within a detent of the regulating plate. Registration of one or more of the bores provides a visual indication of a level of dispensing intensity.

In yet another aspect, a dispenser includes a volatile material containing reservoir and a cover having at least one aperture and a series of ports. A regulating plate is operatively attached to the cover and has at least one window and a series of bores. The series of ports and bores have a different geometric shape than the at least one window.

BRIEF DESCRIPTION OF THE DRAWINGS

FIG. 1 is an isometric view of a front, top, and side of a volatile material dispenser;

FIG. 2 is a side elevational view of the volatile material dispenser of FIG. 1;

FIG. 6 is a sectional view of the volatile material dispenser of FIG. 1 taken generally along the line 6-6 of FIG. 1;

FIG. 7 is a sectional view of the volatile material dispenser of FIG. 1 taken generally along the line 7-7 of FIG. 1;

FIG. 7A is a sectional view of the volatile material dispenser similar to FIG. 7, having a different cartridge therein;

FIG. 9A is a sectional view of the volatile material dispenser of FIG. 9, with a different cartridge therein;

DETAILED DESCRIPTION

Figure 3:
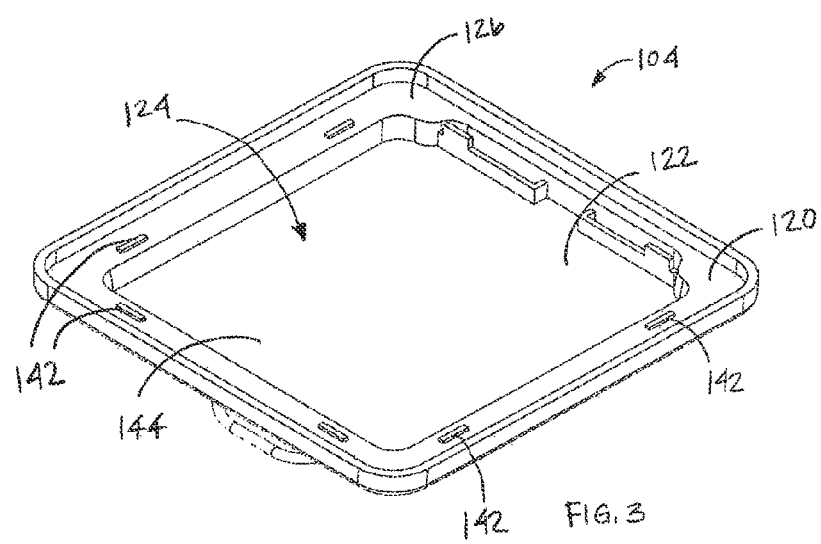
FIG. 3 is an isometric view of a base of the volatile material dispenser of FIG. 1.

Referring to FIGS. 1-10, a volatile material dispensing system 100 includes a dispenser 102, which generally includes a base 104 and an interchangeable cover 106. The cover 106 attaches to the base 104 to define a chamber 108 therebetween. A refill cartridge 110 is held within the chamber 108 (see FIGS. 6-7A) and includes a reservoir 112 having a volatile material therein. The dispenser 102 also includes a regulating plate 114 mounted under the cover 106 such that the regulating plate 114 is movable relative to the cover 106.

Figure 4:
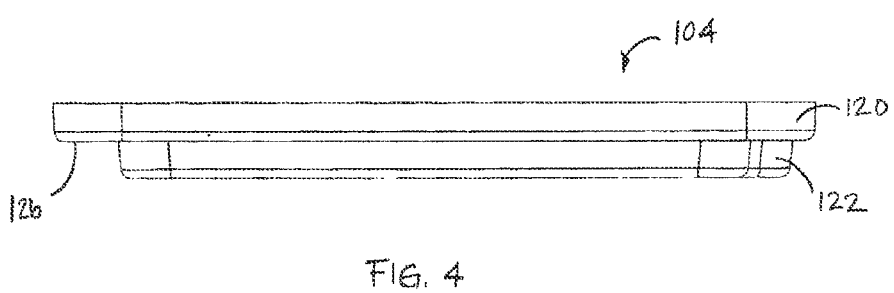
FIG. 4 is a side elevational view of the base of FIG. 3.
Figure 5:
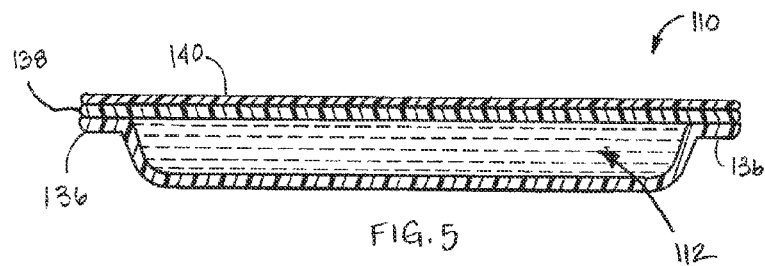
FIG. 5 is a sectional view of a cartridge for use in the dispenser.

Referring to FIGS. 3 and 4, the base 104 generally includes an upper body portion 120 and a lower body portion 122. The lower body portion 122 depends from the upper body portion. 120 and defines a recess 124 therein. The upper body portion 122 includes a shelf 126 that extends about an upper perimeter of the lower body portion 122. The base 104 therefore comprises a stepped-in profile, which creates the illusion that the dispenser 102 has a lower visual weight than prior art dispensers. Specifically, the visual weight when viewed from the sides about an axis Y, or at an angle thereto, is greatly decreased. For example, as shown in FIG. 1, the base 104 is not visible when the dispenser 102 is viewed at an angle from above and to the side. The lighter appearance of the dispenser 102 is more aesthetically pleasing to users than prior, bulkier appearing dispensers.

The refill cartridge 110 is similar to those described in U.S. Pat. No. 7,441,360. As shown in FIGS. 5-7A, the cartridge 110 includes a flange 136 surrounding the reservoir 112. A permeable membrane 138 is adhered to the flange 136 to cover the reservoir 112 and extends across the cartridge 110. As noted above, the reservoir 112 is filled with a volatile material, which may comprise an active ingredient for diffusion into the surrounding atmosphere, such as a fragrance, air freshener, odor eliminator, or insect repellant. It is contemplated that any type of volatile material suited for dispersal through the permeable membrane 138 may be used with the present embodiments described herein. An impermeable laminate 140 is releasably adhered to the cartridge 110 over the permeable membrane to prevent release of the volatile material prior to use. Although the cartridge of the present embodiment has a single reservoir 112, it is contemplated that cartridges having two or more reservoirs filled with the same or different volatile materials may be used.

In use, as best illustrated in FIGS. 6-7A, the cartridge 110 is inserted within the base 104 such that the reservoir 112 aligns within the recess 124 in the lower portion 122 of the base 104. The flange 136 rests on a plurality of ribs 142 disposed on the shelf 126 around the recess 124. The ribs 142 assist in maintaining the proper alignment of the cartridge 110 within the dispenser 102, such that a portion of the refill cartridge 110 is retained at a constant distance H from a distal most portion of the regulating plate 114. In the present embodiment, the distance H is a line that is perpendicular to a plane defined by the permeable membrane 138 and is measured between an inner surface of the most distal portion of the regulating plate, i.e., the portion(s) of the regulating plate farthest from the cartridge 110, and the plane defined by the permeable membrane 138. In some embodiments, the distance H may be constant about the entirety of the cartridge or reservoir, whereas in other embodiments, e.g., such as the one shown in FIGS. 1-10, the distance H may be measured at a discrete point, e.g., the apex of the domed regulating plate shown in FIGS. 7 and 7A. Preferably, the distance H is between about 0.25 mm to about 10 mm, and more preferably between about 0.5 mm to about 3 mm.

Turning to FIG. 7, a 12 gram refill cartridge 110 is depicted, in which the reservoir 112 rests on a bottom surface 144 of the recess 124 such that the permeable membrane 138 of the refill cartridge 110 is maintained a distance H from the distal most portion of the inner surface of the regulating plate 114. However, if a smaller refill cartridge 110 is used, such as the 8 gram refill cartridge 110 shown in FIG. 6A, the reservoir 112 of the cartridge 110 would be too small to rest on the bottom surface 144 of the recess 124 and still maintain the same distance H between the cartridge 110 and the cover 106 without the ribs 142. Thus, the ribs 142 allow different sized refill cartridges 110 to be used within the same dispenser 102. The ribs 142 also raise the flange 136 above the shelf 126, thereby creating a gap 146 between the shelf 126 and the flange 136 to provide a user with a way to grasp the flange 136 and remove the cartridge 110 from within the base 104.

In a preferred embodiment, the flange 136 is captured between the ribs 142 and an inner surface of one or more of the cover 106 and the regulating plate 114 to securely retain the cartridge 110 within the dispenser 102. In another preferred embodiment, the flange 136 is loosely retained between the ribs 142 and the cover 106 and/or regulating plate 114, so that the cartridge 110 may move within the dispenser 102. However, the distance H in either embodiment is measured, as noted above, when the flange 136 is resting on the ribs 142.

In the present embodiment, the reservoir 112 of the cartridge 110 has a similar shape as the recess 124 of the base 104, which provides improved refill cartridge orientation within the dispenser 102 by providing a clear indication to the user of the proper way to insert the refill cartridge 110. Further, having a similarly shaped cartridge 110 and recess 124 also prevents the refill cartridge 110 from substantially moving when the dispenser 102 is assembled and being used. However, it is contemplated that refill cartridges 110 with reservoirs 112 shaped differently than the recess 124 may be used in alternative embodiments.

Figure 8:
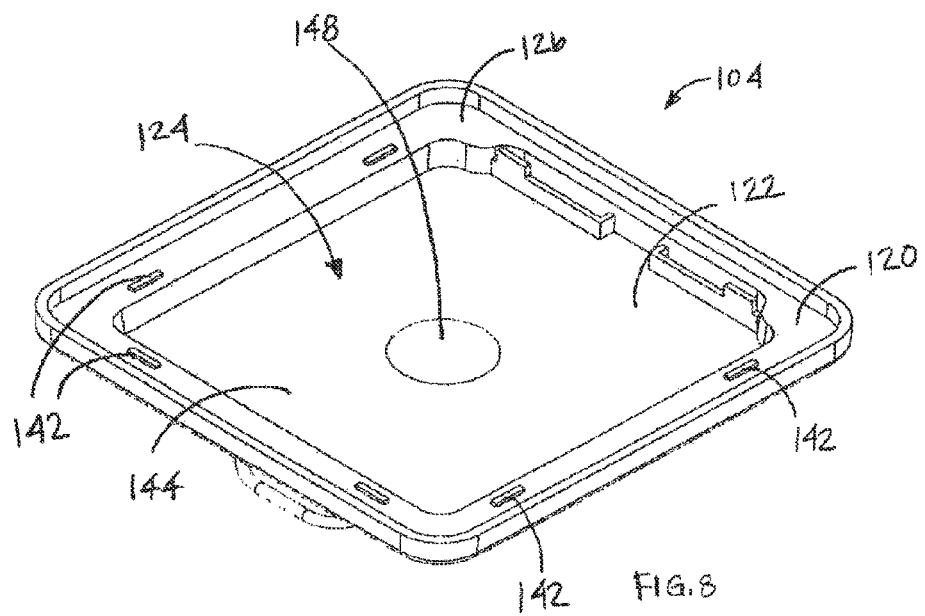
FIG. 8 is an isometric view of an alternative base for the volatile material dispenser of FIG. 1.
Figure 9:
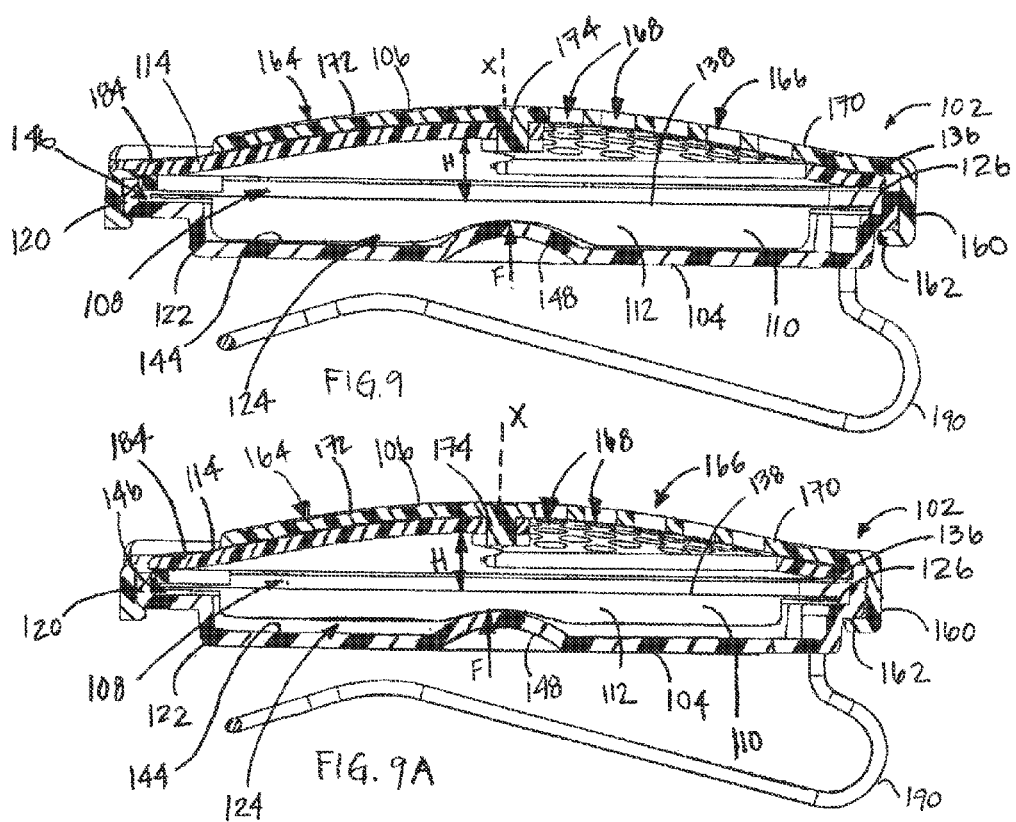
FIG. 9 is a sectional view similar to that of FIG. 7, having the base of FIG. 8.

Referring to FIGS. 8-9A, the base 104 is shown to optionally include a domed portion 148 disposed on the bottom surface 144 of the base 104. The domed portion 148 assists in the proper placement of the refill cartridge 110 within the dispenser 102 and in managing any size variations between different refill cartridges 110. In use, the domed portion 148 contacts a bottom portion of the reservoir 112 to prevent the cartridge 100 from resting too low within the recess 124. The domed portion 148 thereby assists in holding the cartridge 100 at the preferred distance H from the cover 106, regardless of the size of the refill cartridge 110 (see FIGS. 9 and 9A). The domed portion 148 also provides a force F against the reservoir 112 of the cartridge 110, which causes the reservoir 112 to deflect inwardly. The deflection of the reservoir 112 assists in transferring the volatile material within the refill cartridge 110 toward the permeable membrane 136 to aid in the diffusion of the volatile material from the cartridge 102. Additionally, the force F from the domed portion 148 against the reservoir 112 also assists in distributing the volatile material to peripheral portions of the reservoir 112 to prevent pooling of the volatile material within the center of the cartridge 110.

In an alternative embodiment, rather than deflecting inwardly, the reservoir 112 may include a corresponding domed recess 148 (see alternative domed recess 148' in FIG. 10) that aligns with the domed portion 148 of the base 104. The corresponding domed portions 148, 148' provide an indication to the user of the proper orientation of the refill cartridge 110 during insertion. Further, the corresponding domed portions 148, 148' may act as a lock and key mechanism to prevent improper refill cartridges 110 from being inserted into the dispenser 102, which could damage the dispenser 102 or cause the dispenser to work improperly. Alternatively, the domed portions 148, 148 may be provided in any complementary shape.

After the refill cartridge 110 is inserted into the base 104 and the impermeable laminate 140 is removed, the cover 106 is then mounted onto the base 104 over the cartridge 110. The cover 106 includes two wings 160 depending from opposing ends of the cover 106. The wings 160 include inwardly extending flanges 162 that attach below the upper body portion 120 of the base 104 to achieve a releasable attachment of the cover 106 to the base 104 by way of a snap-fit connection. Alternatively, the flanges 162 may be attached by friction fit to the base 104 or the cover 106 may be alternatively secured to the base by any other means known to one of ordinary skill.

A user can separate the cover 106 from the base 104 by applying sufficient force to portions of the wings 160 extending below the flanges 162, which cause the flanges 162 to deflect out from below the upper body portion 120 of the base 104. The cover 106 may thereafter be removed from the base 104. After separation of the cover 106 from the base 104, a user may replace an exhausted refill cartridge 110 with a new cartridge. Additionally, the user may remove the cover 106 and replace it with an alternative cover 106 depending on user preferences as relates to aesthetics and performance. Further, the symmetry between the base 104 and the cover 106 allows the user to attach the cover 106 to the base 104 in any orientation.

Figure 10:
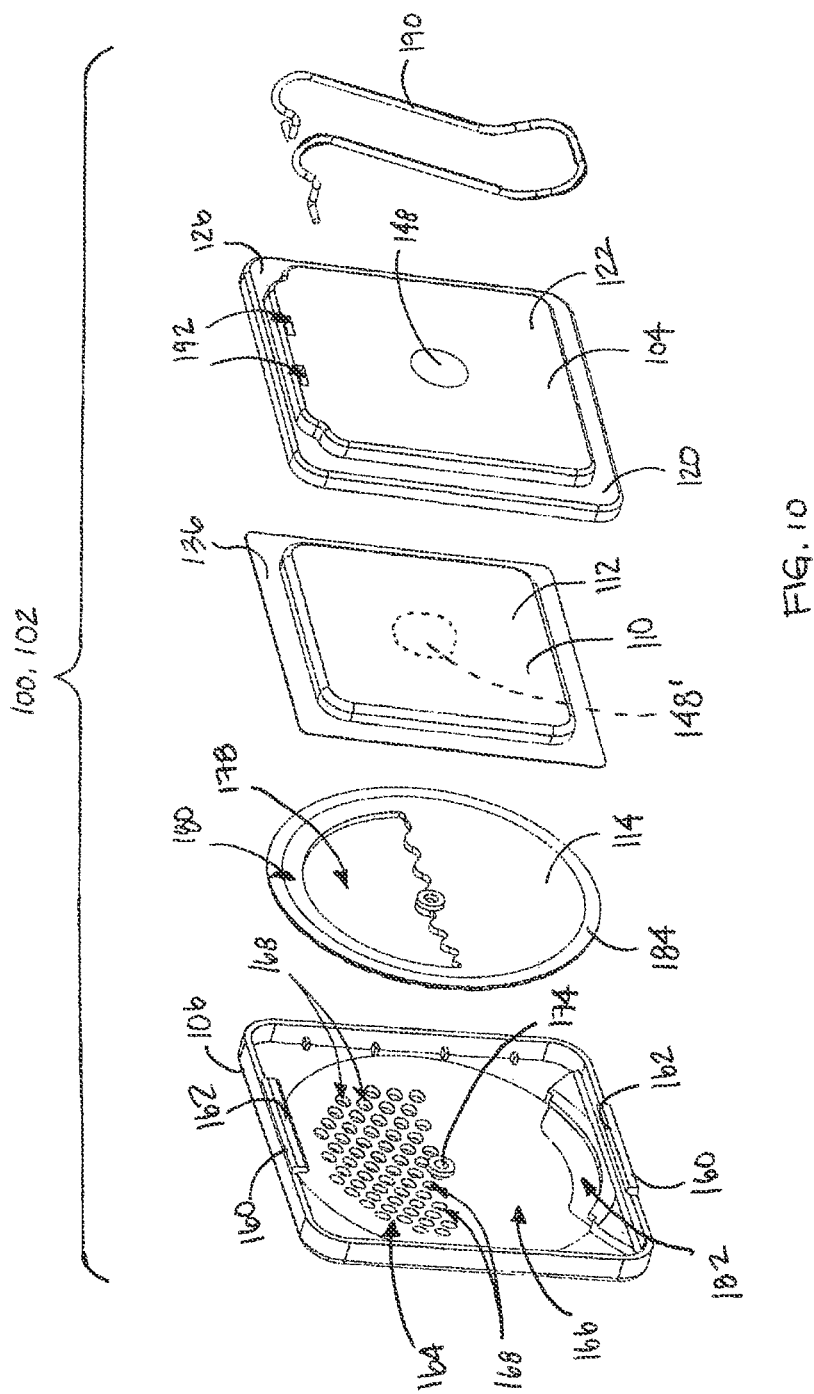
FIG. 10 is an exploded bottom isometric view of the volatile material dispenser of FIG. 1.

Referring now to FIGS. 1, 2, and 10, the cover 106 comprises a first portion 164 that includes bores, holes, or apertures and a second portion 166 that does not include any bores, holes, or apertures. In one particular embodiment, the first portion 164 may include any number of apertures 168, e.g., one or more. The apertures 168 may comprise any geometric shape or size. Preferably, the apertures 168 comprise between about 2% to about 50% and more preferably between about 5% to about 25% of the total surface area A of a top surface 170 of the cover 106.

In the present embodiment, the cover 106 has a plurality of circular apertures 168 disposed in a generally half-moon arrangement within the first portion 164. The present embodiment also includes a plurality of decorative circles 172 indented into the second portion 166 of the cover 106. As shown in FIGS. 7-7A, the cover 106 also includes a post 174 depending from an underside thereof. The post 174 is designed to receive the regulating plate 114 thereon and defines an axis of rotation X of the regulating plate 114. The regulating plate 114 is circular with a generally half-moon shaped window 178 disposed in a first half 180 thereof. The cover 106 further includes an arc-shaped opening 182 within the second portion 166 of the cover 106. In the present embodiment, the cover 106 and the regulating plate 114 are both slightly domed, however, it is contemplated that the cover 106 and the regulating plate 114 may be flat to minimize the internal and/or external volume of the dispensing system 100. Indeed, the cover 106 and the regulating plate 114 may have varying shapes so long as the regulating plate 114 is disposed adjacent to the cover 106 when attached.

When the regulating plate 114 is attached to the cover 106, a peripheral portion 184 of the regulating plate 114 extends through the arc-shaped opening 182 in the cover 106. The peripheral portion 184 allows the user to adjust the diffusion of the volatile material as discussed below. The peripheral portion 184 of the regulating plate 114 may also include a plurality of grooves 186 to assist the user in locating and adjusting the regulating plate 114.

In use, the regulating plate 114 rotates around the axis of rotation X between an open position and a closed position when the peripheral portion 184 of the regulating plate 114 is moved by a user within the arc-shaped opening 182. The regulating plate 114 is in the closed position when the window 178 is aligned with the second portion 166 of the cover 106. Thus, all of the apertures 168 are covered when the regulating plate 114 is in the closed position, thereby preventing the volatile material of the cartridge 110 from being released through the apertures 168 into the surrounding atmosphere. In the open position, the window 178 is completely aligned with the apertures 168 in the cover 106. Thus, in the open position the volatile material from the cartridge 110 can be dispensed through the apertures 168 into the surrounding atmosphere. Additionally, the regulating plate 114 can be located in a partially open position, which is somewhere between the open and closed positions. When the regulating plate 114 is in a partially open position, a portion of the window 178 is aligned with the apertures 168 in the cover 106. When the regulating plate 114 is in a partially open position, the dispensing rate of the volatile material is somewhere between the rates of dispensing found in the open position and the closed position due to the partial coverage of the first portion 164. Aligning a greater portion of the window 178 with the apertures 168 will increase the dispensing rate of the volatile material from the dispenser 102. As such, the user can control the amount of volatile material being released from the dispenser 102 by rotating the regulating plate 114.

Figure 11:
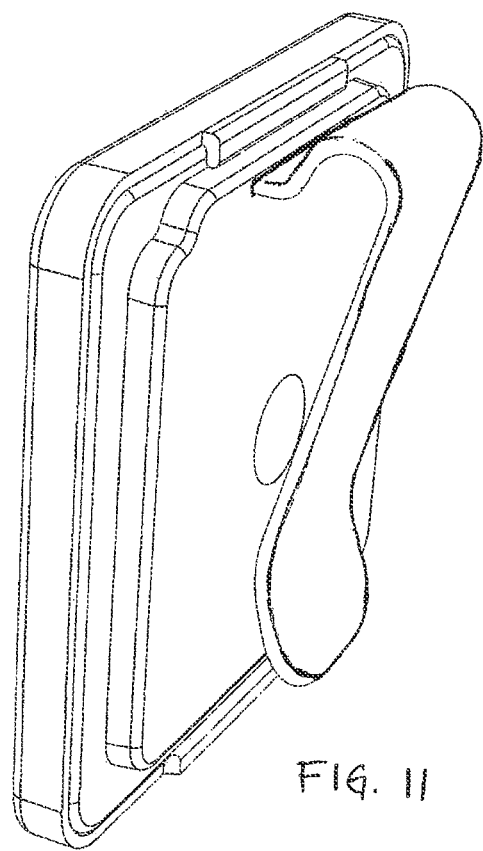
FIG. 11 is a bottom isometric view of the volatile material dispenser of FIG. 1, with a different clip.

The dispenser 102 may also include a mounting clip 190, which allows the dispenser 102 to be attached to a visor of a car. The mounting clip 190 may be made of a bent wire, a formed wire, formed plastic, and the like. In the present embodiment, the mounting clip 190 is a bent wire that is releasably inserted into apertures 192 disposed in a bottom of the base 104. The mounting clip 190 can be removed from the base 104 so that the dispenser 102 may rest flat on a surface. In one particular embodiment, the mounting clip 190 comprises a conventional visor clip, which is commonly used in connection with securing a garage door opener to a car visor (see FIG. 11). Indeed, any type of clip may be used in connection with any of the dispensing system embodiments disclosed herein.

Figure 12:
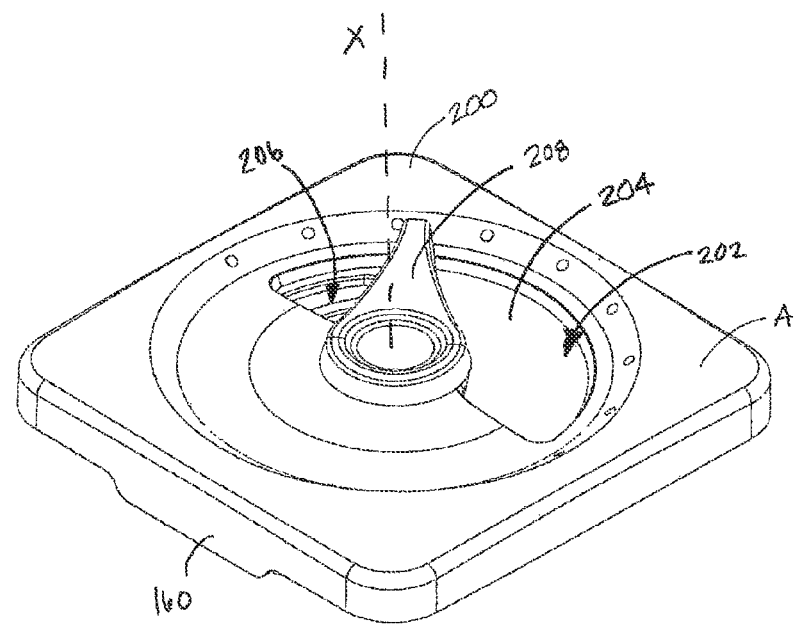
FIG. 12 is a top isometric view of an alternative cover for a volatile material dispenser.
Figure 12A:
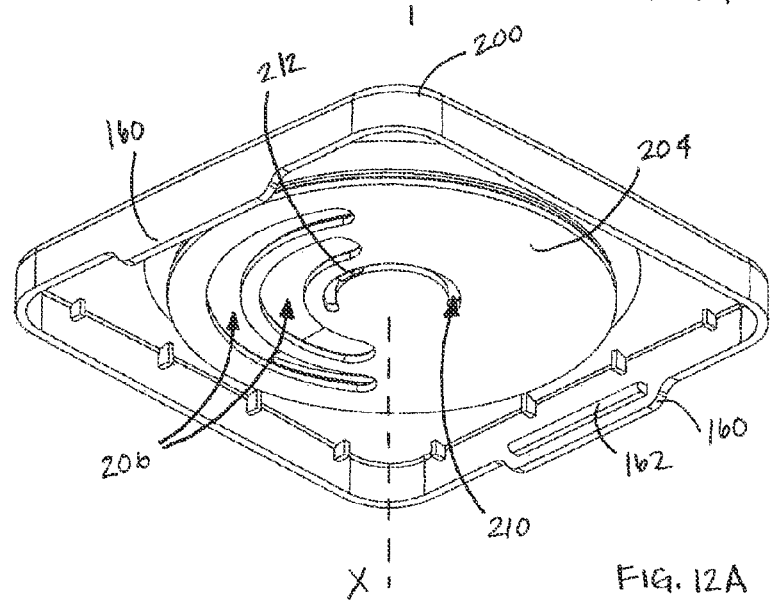
FIG. 12A is a bottom isometric view of the cover shown in FIG. 12.

The base 104 of the present dispensing system 100 is not limited to use with the cover 106 shown in FIGS. 1-10. Rather, the base 104 may be used with a variety of interchangeable covers such as those shown in FIGS. 12-15A. FIGS. 12 and 12A illustrate one alternative cover 200 for use in the dispensing system 100. The cover 200 includes a single half-moon shaped aperture 202. A circular regulating plate 204 is rotatably attached to the cover 200 and is capable of rotating around a centrally located axis of rotation X. The regulating plate 204 includes two arc-shaped windows 206 and an adjustment tab 208 extending through the cover 200. The adjustment tab 208 provides the user with the ability to adjust the dispensing rate of the dispenser 102 and provides a visual break between the windows 206 and the remainder of the regulating plate 204. A user can control the dispensing rate of the dispenser 102 by rotatably moving the adjustment tab 208 and regulating plate 204 around the axis of rotation X between an open position, in which the windows 206 completely align with the aperture 202, and the closed position, in which the aperture 202 is completely covered by the regulating plate 204. As seen in FIG. 12A, the regulating plate 204 also includes a semi-circular guide slot 210 disposed around the axis of rotation X. The guide slot 210 receives a tab 212 depending from the cover 200. The combination of the tab 212 and the guide slot 210 assists in guiding the rotation of the regulating plate 204. Additionally, the tab 212 and guide slot 210 also acts as a stop that informs the user when the dispenser 102 is in the fully open or closed positions, i.e., the tab 212 abuts against distal portions of walls defining the slot 210 in the open and closed positions.

Figure 13:
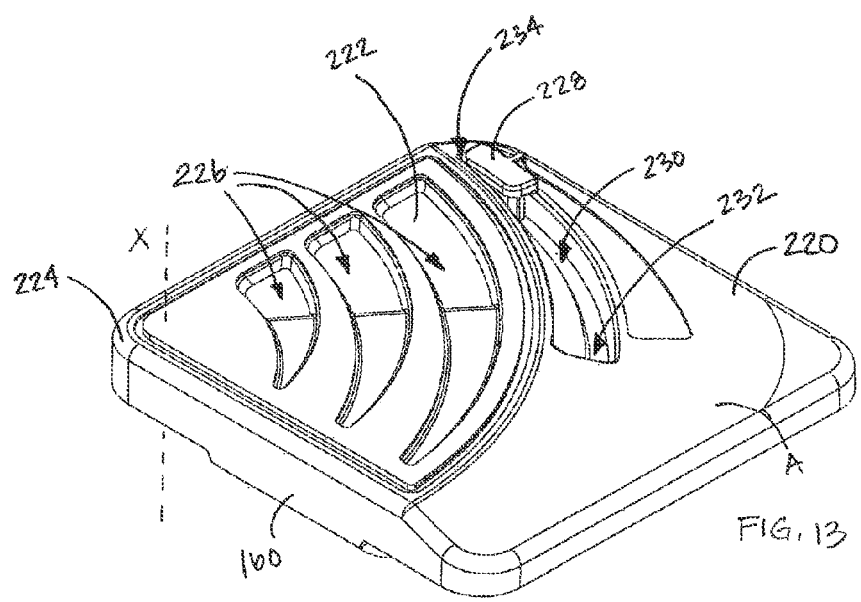
FIG. 13 is a top isometric view of a further alternative cover for a volatile material dispenser.
Figure 13A:
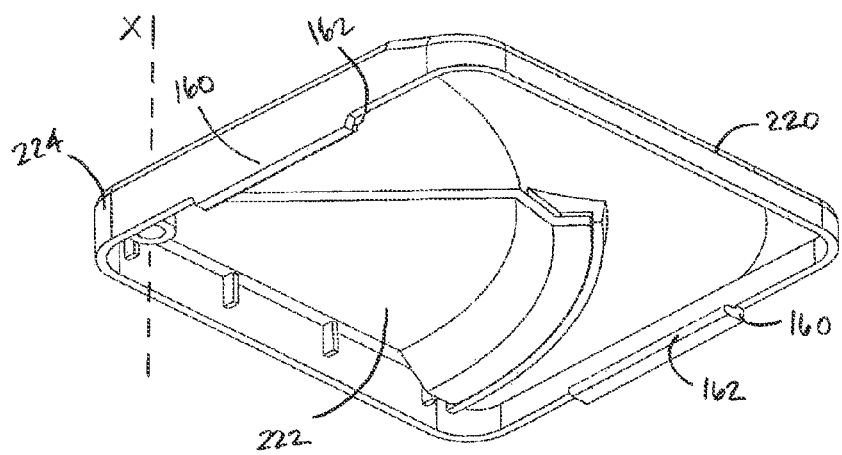
FIG. 13A is a bottom isometric view of the cover shown in FIG. 13.

In an alternative embodiment shown in FIGS. 13 and 13A, a cover 220 includes a regulating plate 222. The regulating plate 222 has an axis of rotation X located adjacent a corner 224 of the cover 220. The cover 220 includes three curved apertures 226. The regulating plate 222 is fan-shaped and includes an adjustment tab 228 extending through an arc-shape guide slot 230 in the cover 220. The regulating plate 222 is rotatable between an open position, in which the adjustment tab 228 is located at a first end 232 of the guide slot 230, and a closed position, in which the adjustment tab 228 is located at a second end 234 of the guide slot 230. In the closed position, the apertures 226 are covered by the regulating plate 222 (see FIG. 13).

Figure 14:
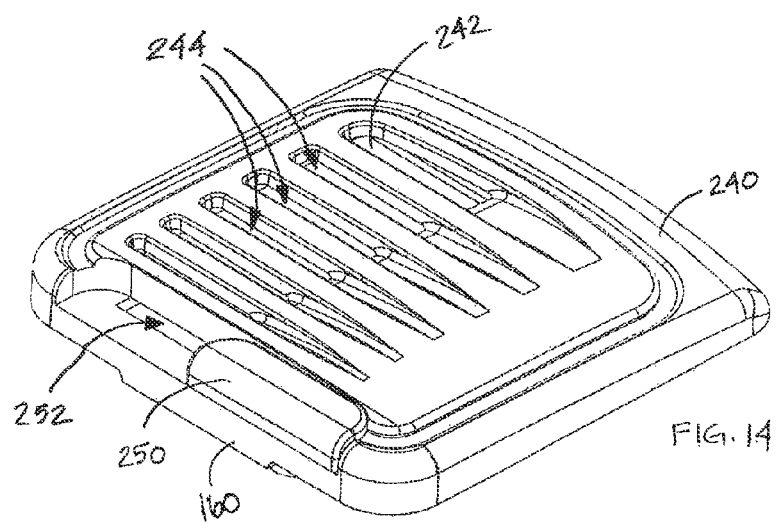
FIG. 14 is a top isometric view of a still further embodiment of a cover for a volatile material dispenser.
Figure 14A:
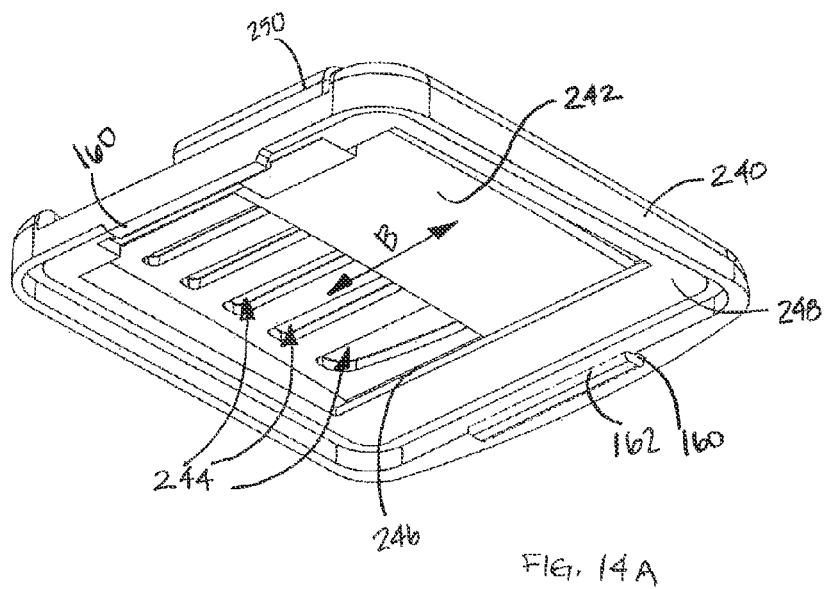
FIG. 14A is a bottom isometric view of the cover shown in FIG. 14.

Yet another embodiment of a cover 240 is illustrated in FIGS. 14 and 14A. The cover 240 includes a rectangular regulating plate 242 that does not rotate relative to the cover 240. Rather, the plate 242 slides in a substantially straight line relative to the cover 240, as illustrated by arrow B. The cover 240 includes a plurality of generally rectangular apertures 244 disposed within one half of the cover 240. Guide slots 246 are provided within an underside 248 of the cover 240, which allows the regulating plate 242 to slide between open and closed positions. The regulating plate 242 also includes an adjustment tab 250 that extends through a guide slot 252 in the cover 220 to allow the user to easily move the regulating plate 242 between the open and closed positions.

Figure 15:
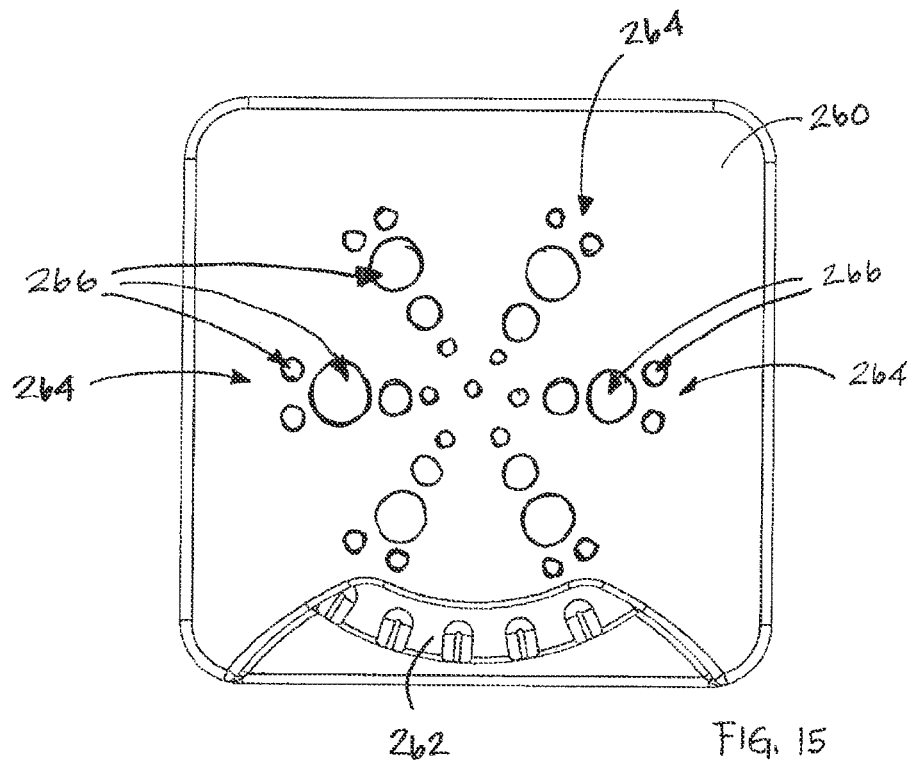
FIG. 15 is a top plan view of another embodiment of a cover for a volatile material dispenser.
Figure 15A:
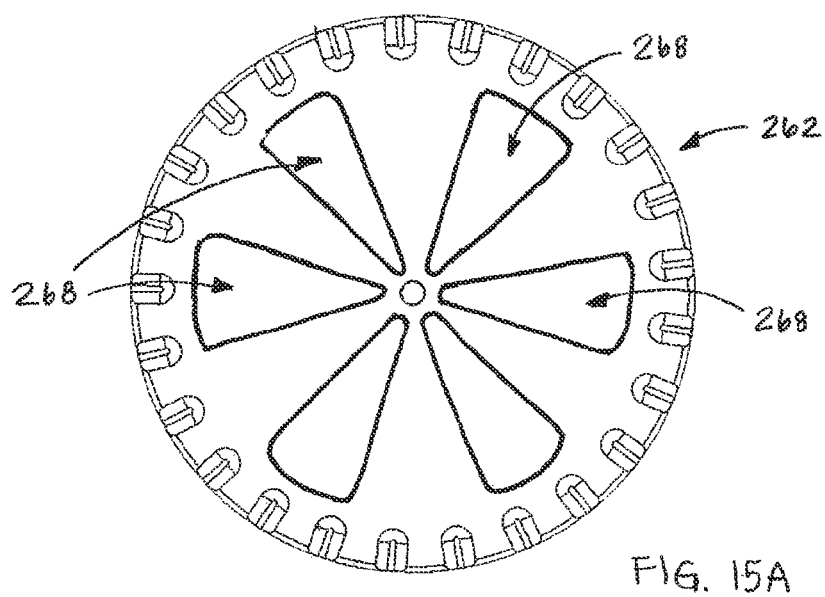
FIG. 15A is a top plan view of a regulating plate for the cover of FIG. 15.

FIGS. 15 and 15A illustrate another embodiment of a cover 260 and regulating plate 262. The cover includes a plurality of sections 264 containing circular apertures 266 therein. The circular regulating plate 262 is rotatably attached to the cover 260 and includes a plurality of windows 268 disposed therein. The number of windows 268 in the regulating plate 262 corresponds to the number of sections of apertures 264 in the cover, such that each window 268 aligns with a section of apertures 264 in an open position. A user may rotate the regulating plate 262 from the open position to a closed position, in which the apertures 266 are covered by the regulating plate 262. Moving the plurality of windows 268 concurrently, as opposed to a single window within a regulating plate as shown above, increases the ratio of the opening speed of the dispenser in relation to the distance the regulating plate 262 moves. As such, the user is able to open and/or close the dispenser with less effort. Further, the plurality of windows 268 increases the strength of the regulating plate 262 compared to regulating plates that include one large window or hole therein.

Figure 16:
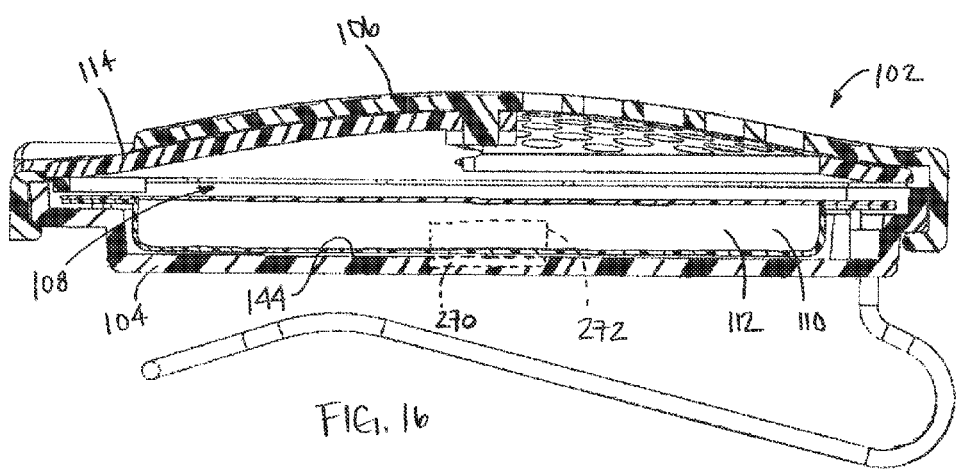
FIG. 16 is a sectional view similar to that of FIG. 7, with a different base and cartridge therein.

Turning to FIG. 16, another alternative embodiment is shown that is similar to FIG. 7, except for the inclusion of a first magnetic element disposed within the base 104. The first magnetic element 270 may be provided on an inside, outside, or within a portion of the base 104 and is adapted to functionally interact with a second magnetic element 272 on or within the cartridge. For example, various possible exemplary embodiments and descriptions of the functional interaction of magnetic elements within dispensers and cartridges are shown in U.S. application Ser. No. 12/896,583. For example, in the present embodiment the first magnetic element 270 is disposed within the bottom surface 144 of the base 104 and the second magnetic 272 element is disposed within the reservoir 112 of the cartridge 110. The first and second magnetic elements 270, 272, respectively, shown in FIG. 16 may be utilized in connection with any of the embodiments disclosed herein.

An alternative embodiment of a volatile material dispenser 300 is shown in FIGS. 17-24. The dispensing system 300 is similar to the dispensing system 100, except for the differences noted herein. Further, it is contemplated that various embodiments described in the following paragraphs can be combined or interchanged with various embodiments related to the dispensing system 100.

Referring to FIGS. 17-24, the alternative dispensing system 300 includes a dispenser 302 having a base 304 and an interchangeable cover 306. The cover 306 attaches to the base 304 to define a chamber 308 therebetween. The chamber 308 (see FIG. 24) receives a volatile material refill cartridge, such as the previously presented refill cartridge 110 having the reservoir 112 with the volatile material therein (see FIG. 5). The dispenser 302 further includes a regulating plate 310 mounted under the cover 306 such that the regulating plate 310 is movable relative to the cover 306. The regulating plate 310 allows the user to select a level of diffusion intensity of the volatile material by exposing more or less of the refill cartridge to the external surroundings. Further, the regulating plate 310 provides additional holes that facilitate additional diffusion of the volatile material and provide a visual indication to the user on the amount of volatile material that the dispenser 302 is releasing.

Figure 19:
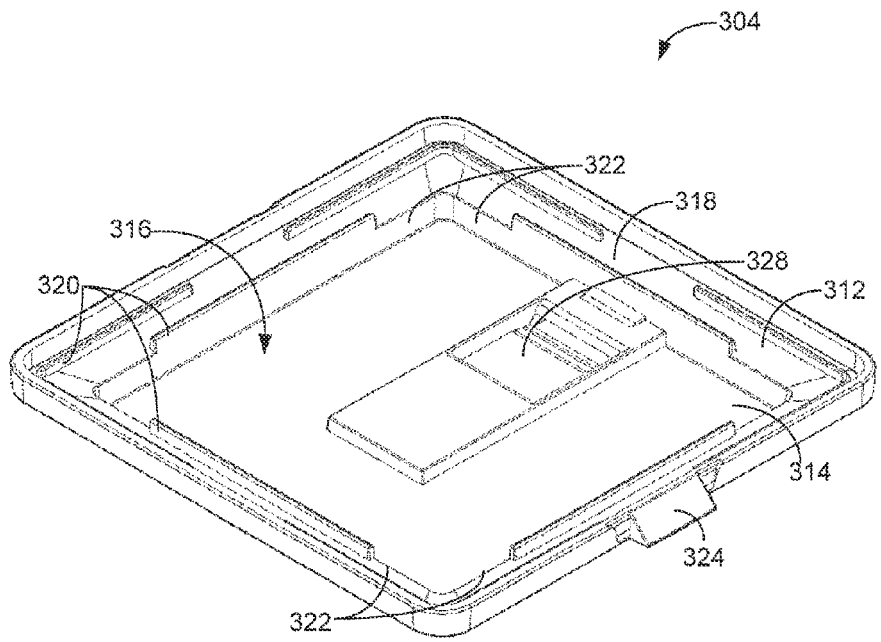
FIG. 19 is an isometric view of a base of the volatile material dispenser of FIG. 17.
Figure 20:
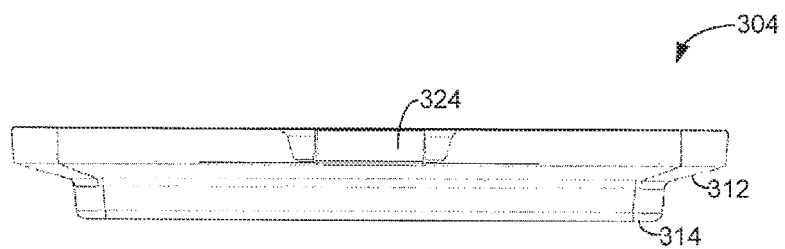
FIG. 20 is a side elevational view of the base of FIG. 19.

Referring to FIGS. 19 and 20, the base 304 of the dispenser 302 generally includes an upper body portion 312 and a lower body portion 314. The lower body portion 314 depends from the upper body portion 312 and defines a recess 316 therein. The upper body portion 312 includes a shelf 318 that extends about an upper perimeter of the lower body portion 312. The base 304 therefore comprises a stepped-in profile, which creates the illusion that the dispenser 302 has a lower visual weight than prior art dispensers. The stepped-in profile is further adapted to receive the refill cartridge 110, which also forms a stepped-in profile by way of the reservoir 112 surrounded about its upper edge by the extending flange 136 (see FIG. 5). In operation, the reservoir 112 of the cartridge 110 is placed in the recess 316 of the base 304 such that the flange 136 rests on a plurality of longitudinal ribs 320, which project upwardly from the surface of the shelf 318 surrounding the recess 316. As shown in FIG. 19, a total of eight longitudinal ribs 320 are staggered on the shelf 318, whereby four of the ribs 320 wrap around the corners of the base 304 and another four ribs 320 are aligned parallel with four sidewalls 322. In one aspect, staggering the longitudinal ribs 320 at various depths and regions of the shelf 318, such as ribs 320 placed at varying distances from the edges of the recess 316 as demonstrated in FIG. 19, allow the base 304 to accommodate refill cartridges 110 having different flange 136 and/or reservoir 112 sizes.

The base 304 further provides means for securing the cover 306 thereon, such as a pair of flaps 324 protruding outwardly from two opposing sides of the upper body portion 312. The flaps 324 are adapted to be press fit or latched with corresponding mating parts provided on the cover 306, such as a pair of wings 334 (see FIGS. 17 and 18), to securely attach the cover 306. It is contemplated that the flaps 324 are resilient and flexible to withstand multiple attachments and removals of the cover 306 and provide easy access for replacing the refill cartridge 110 throughout the lifetime of the dispenser 302. Turning again to FIG. 19, the base 304 further comprises a slot 328 integrally formed on the lower body portion 314 for insertion of a mounting clip 330, which may be utilized for mounting the dispenser 302 onto a visor of an automobile. The mounting clip 330 is slidingly received in the slot 328 and is locked in by engaging a projection 332 provided on the underside of the base 304 (see FIG. 23), in the present embodiment, the mounting clip 330 is a bent metallic strip with a bore for hookingly engaging the projection 332. Various locking means can be contemplated to prevent the mounting clip 330 from slipping out of the slot 328, while still providing the user the option to remove the clip 330 and thereby deploy the dispenser 302 on a flat surface, such as a table-top or dashboard of a car. In another aspect, different clips 330 may be used, such as magnetic clips for attracting the dispenser 302 onto a magnetic surface, and so on.

Figure 17:
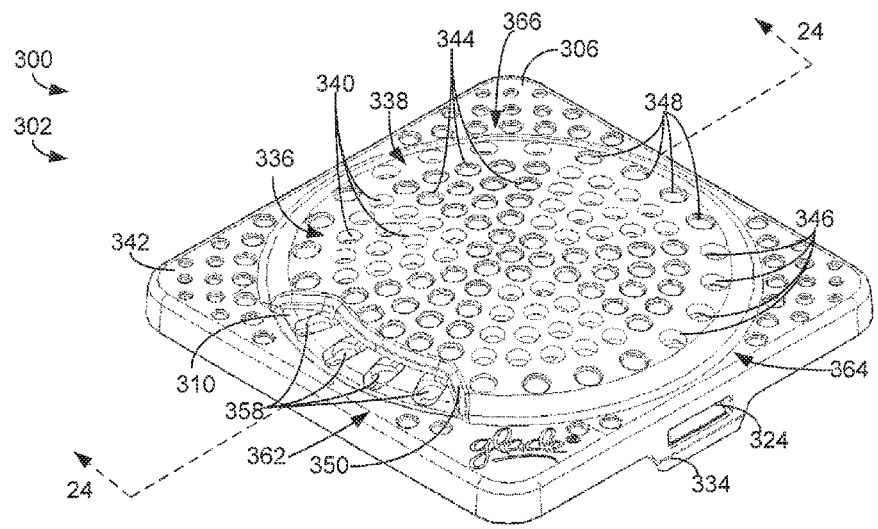
FIG. 17 is an isometric view of a front, top, and side of another embodiment of a volatile material dispenser.
Figure 18:
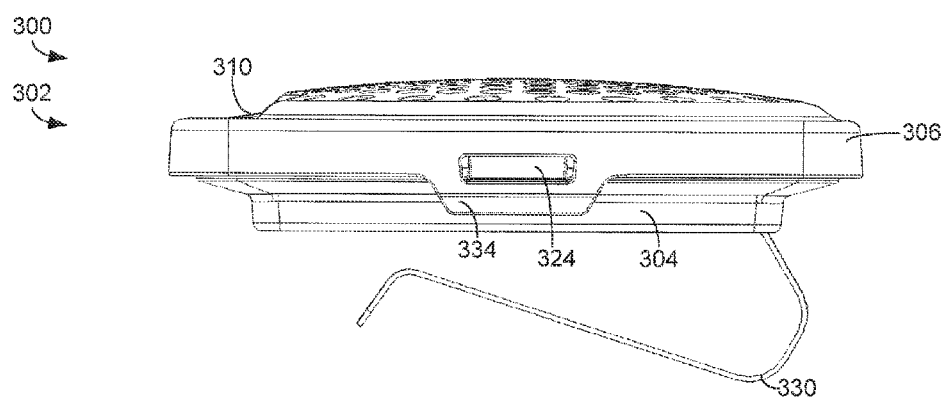
FIG. 18 is a side elevational view of the volatile material dispenser of FIG. 17.
Figure 21:
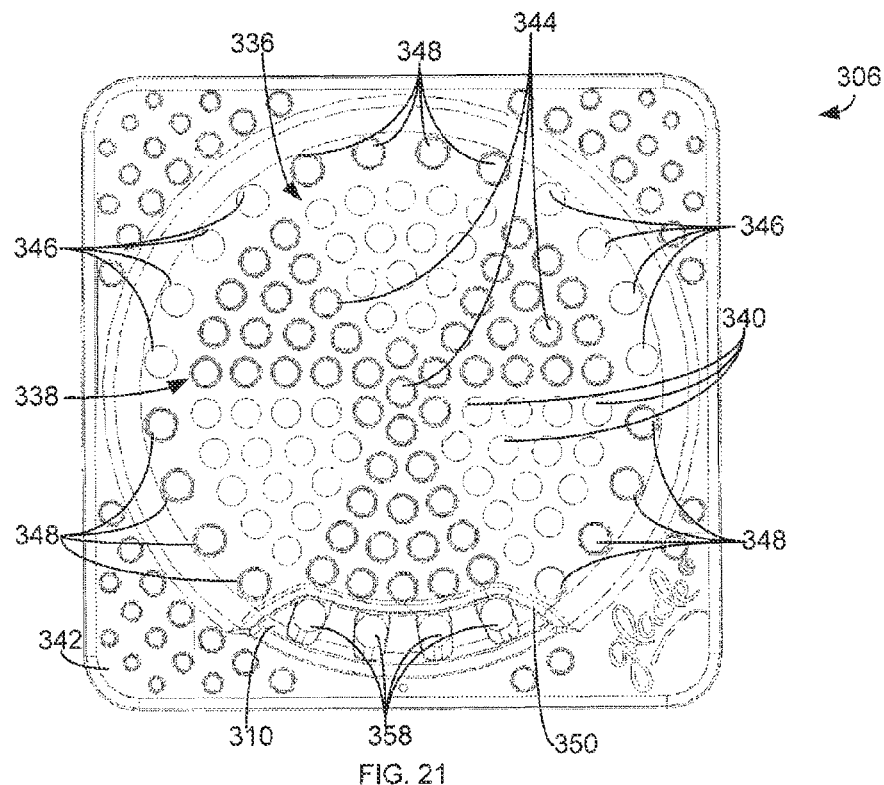
FIG. 21 is a top view of the volatile material dispenser of FIG. 17.

Referring to FIGS. 17, 18, and 21, the cover 306 is a generally curved rectangular surface with two pairs of wings 334 disposed on opposing edges and extending downwardly toward the base 304. The two wings 334 have openings that latch onto corresponding mating parts provided on the base 304, such as the two flaps 324 (see FIGS. 19 and 20). The wings 334 are resilient and may be flexed or temporarily deformed to snap over the flaps 324. To disengage the cover 306 from the base 304, the user simply presses on one or both flaps 324 inwardly to loosen the wings 334 and remove the cover 306.

Turning again to FIGS. 17, 18, and 21, the cover 306 further comprises a first portion 336 and a second portion 338. The first portion 336 is defined by a plurality of apertures 340 that extend through a top surface 342 of the cover 306, while the second portion 338 includes a plurality of decorative circles 344, or other blind holes that do not entirely traverse the thickness of the top surface 342. In the present embodiment, the first portion 336 and the second portion 338 are disposed in an alternating pattern on the top surface 342 of the cover 306, with the second portion 338 extending over the center of the cover 306. Together, the first and second portions 336, 338 define a generally circular zone of diffusion on the top surface 342. The circular zone is bounded by a series of circumferentially disposed open ports 346 that alternate with a series of circumferentially disposed closed ports 348. It is contemplated that the open ports 346 are apertures extending through the top surface 342 and the closed ports 348 are indented, decorative circles provided on the top surface 342. The open ports 346 are configured to align or misalign with corresponding holes on the regulating plate 310, thereby facilitating diffusion of the volatile material through the cover 306 and providing a visual indication to the user on the intensity of the diffusion. The cover 306 further provides an arc-shaped opening 350 disposed in-line with the circumferential ports 346, 348, and particularly disposed between two series of closed ports 348. The arc-shaped opening 350 exposes the circular-shaped regulating plate 310 to allow the user to maneuver the plate 310 and thereby adjust the level of diffusion of the volatile material, as discussed below.

Figure 22:
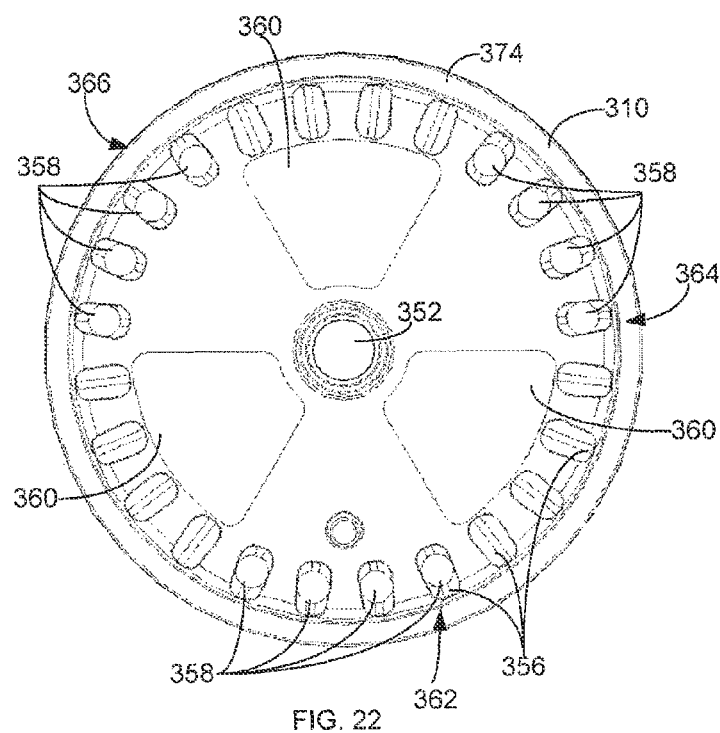
FIG. 22 is a top view of a regulating plate of the volatile material dispenser of FIG. 17.
Figure 23:
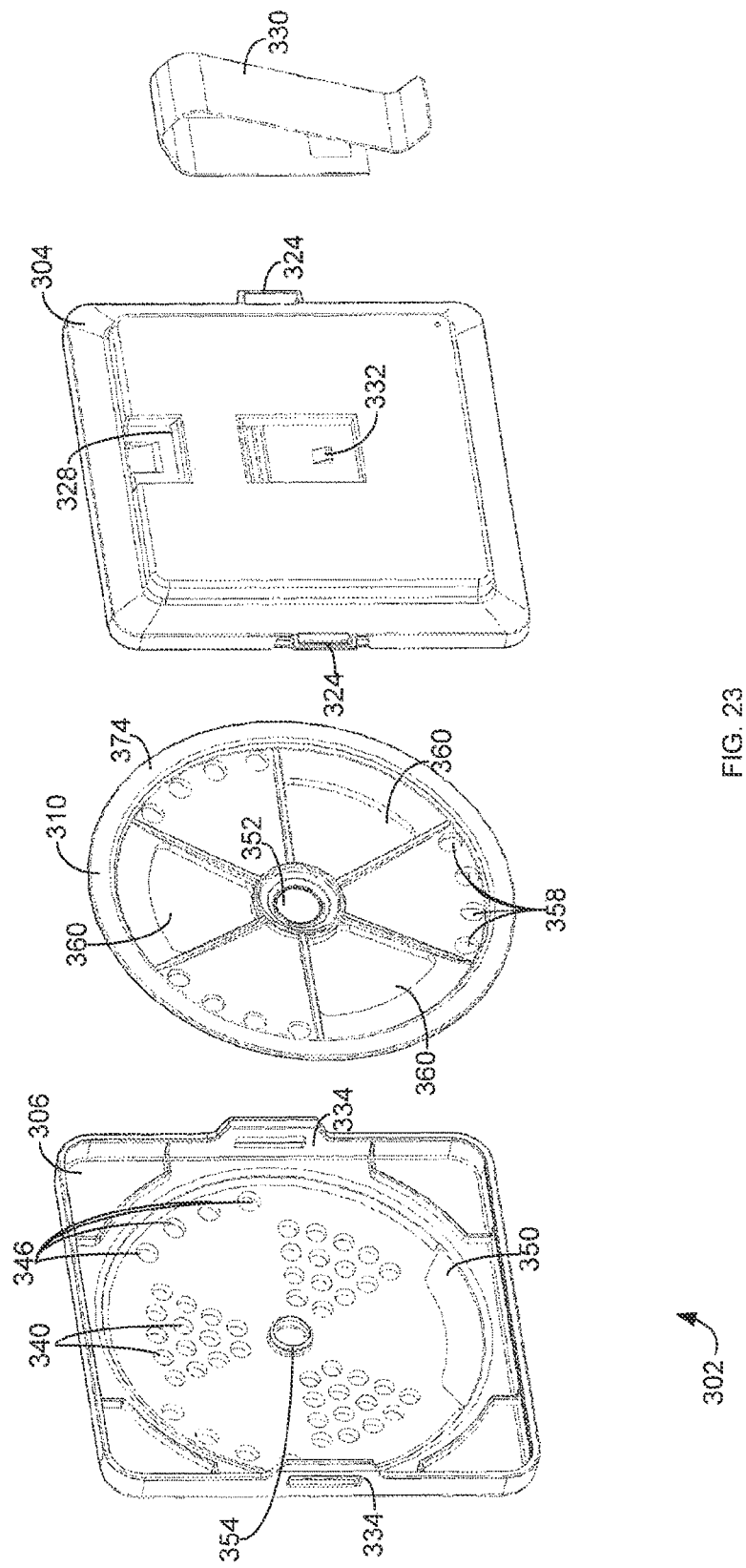
FIG. 23 is an exploded bottom isometric view of the volatile material dispenser of FIG. 17.
Figure 24:
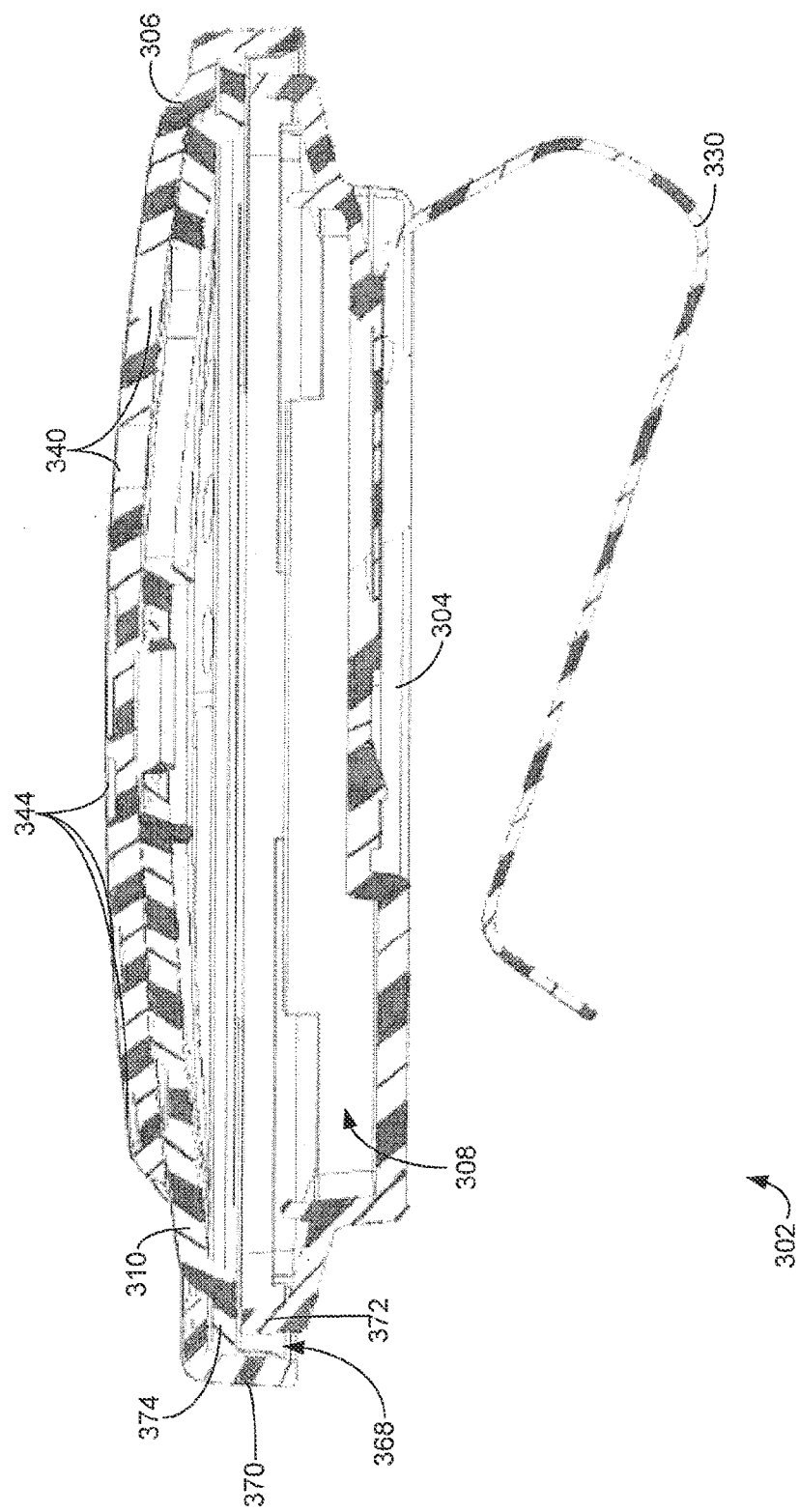
FIG. 24 is a sectional view of the volatile material dispenser of FIG. 17 taken generally along the line 24-24 of FIG. 17.

Referring now to FIGS. 22-24, the regulating plate 310 provides a center hole 352 for rotatably attaching the plate 310 to a post 354 provided on an underside of the cover 306. In operation, the center hole 352 and post 354 define an axis of rotation of the plate 310. A peripheral portion of the regulating plate 310 is exposed through the arc-shaped opening 350. The peripheral, portion includes a plurality of grooves 356 or other detents disposed circumferentially about the periphery of the plate 310 to assist the user in locating and rotating the regulating plate 310. Further, some of the plurality of grooves 356 are provided with bores 358 that traverse through the thickness of the regulating plate 310, thereby exposing the refill cartridge 110 from underneath the plate 310. The regulating plate 310 further provides a plurality of windows 360 that are configured to align with the first portion 336 of the cover 306 in an open position, configured to align with the second portion 338 in a closed, position, and configured to partially span both portions 336, 338 in a partially-open position. For instance, in the particular embodiment as shown in FIG. 22, three windows 360 are spaced apart on the regulating plate 310 in a pattern that is complementary to the pattern of apertures 340 and decorative circles 344 on the cover 306, thus rendering the device capable of providing the completely closed or completely open states of the dispenser 302.

It is further contemplated that the bores 358 are grouped in a pattern that is complementary to the pattern of the windows 360 on the regulating plate 310 and to the pattern of the circumferential ports 348, 346 on the cover 306. In the particular embodiment shown in FIG. 22, a first series 362, a second series 364, and a third series 366 of bores 358 are provided on the peripheral portion of the regulating plate 310 and extend about solid sections of the plate 310 defined between the windows 360. Each series 362, 364, 366 comprises an equal number of bores 358, such as four bores 358. In turn, the peripheral edge of each of the three windows 360 is aligned with four solid grooves 356. In practice, this configuration provides the user with a visual indication of the amount of volatile material being dispensed and further provides additional openings that allow the volatile material to pass through. For instance, in the open position as shown in FIG. 17, the first series 362 of four bores 358 are exposed through the arc-opening 350 of the cover 306, while each of the second series 364 and third series 366 of bores 358 is aligned with a series of four open ports 346 on the cover 306. As such, all of the apertures 340 and the open ports 346 of the cover 306 are aligned with the bores 358 and the windows 360 of the regulating plate 310, such that the dispenser 302 is completely open for maximum diffusion of the volatile material. It is contemplated that the windows 360 operate as the main passageways for dispensing the volatile material, while the bores 358 operate as both passageways for the volatile material and as a visual indication of the dispensing intensity of the volatile material.

Conversely, in the closed position, the regulating plate 310 is rotated such that all of the apertures 340 and the open ports 346 of the cover 306 are misaligned with the bores 358 and the windows 360 of the regulating plate 310. Therefore, no diffusion of the volatile material is permitted in the closed position. The closed position is visually indicated by four solid grooves 356 of the regulating plate 310 exposed in the arc-shaped opening 350 of the cover 306 along with solid grooves 356 blocking each of the open ports 346 of the cover 306. Therefore, no bores 358 are exposed through the cover 306, which visually indicates to the user that the dispenser 302 is in the closed state.

The regulating plate 310 can also be rotated into intermediate positions in which the dispenser 302 is partially open to diffusion. By aligning a greater portion of the bores 358 with the open ports 346 of the cover 306, and thus aligning a greater portion of the windows 360 with the apertures 340, the diffusion intensity increases and thus the dispensing rate of the volatile material increases. For instance, at a low level of diffusion intensity, a total of three bores 358 are visible on the entire cover 306, with one bore 358 exposed in the arc-shaped opening 350 adjacent to three solid grooves 356 and thus two bores 358 aligned with two open ports 346 of the cover 306. As such, the three visible bores 358 allow passage of the volatile material therethrough and visually indicate to the user that the dispensing intensity is set to low. To increase to the next level of dispensing intensity and allow for greater diffusion of the volatile material, the user rotates the regulating plate 310 in the direction that exposes two bores 358 in the arc-shaped opening 350. A third level of dispensing intensity is visually indicated by three bores 358 exposed in the arc-shaped opening 350, while four bores 358 in the arc-shaped opening 350 indicate maximum dispensing intensity. It is noted that the number of bores 358 indicating diffusion intensities is not limiting to the present invention. Further, while the four bores 358 may indicate four discrete levels of diffusion, it is noted that an infinite amount of diffusion levels may be provided. It is further contemplated that the solid grooves 356 are colored differently than the grooves 356 having bores 358 to further distinguish between open, closed, and partially-open states of the dispenser 302.

Turning now to FIG. 24, a cross-section of the dispenser 302 taken along line 24-24 of FIG. 17 is shown. The cover 306 and the regulating plate 310 are layered together and extend convexly outward. The base 304 is generally flat with a stepped-in profile that defines the recess 308 immediately underneath the regulating plate 310. In a particular aspect, the cover 306 is larger than the base 304 such that a gap 368 is defined between a cover sidewall 370 and a base sidewall 372. It is contemplated that the gap 368 permits the regulating plate 310 to have an increased diameter and/or a wide peripheral ridge 374 (see FIGS. 22-24) that extends above and engages with an upper portion of the base sidewall 372. In use, when the user rotates the regulating plate 310, a downward force is also applied to the plate 310. Interaction of the base sidewall 372 and the peripheral ridge 374 of the regulating plate 310 prevents the plate 310 from being accidentally pushed too far into the dispenser 302 or separating from the cover 306.

It is contemplated that other covers and regulating plates having any combination of apertures and windows may be used with any of the dispensers shown herein. It is further contemplated that the user can control the amount of volatile material being released from the dispenser 302 by rotating the regulating plate 310 in accordance with the dispensing level that is visually indicated by the bores 358 and/or the solid grooves 356.

It is also contemplated that one or more of the base, the cover and the regulating plate may be made from an injection molded plastic, e.g., polypropylene. However, they may also be made of other materials, such as metal, glass, paperboard, co-polyester resins, or any other known material. Further, the base, the cover, and the regulating plate may be made of the same or different materials.

It is still further contemplated that the base, the cover, and the regulating plate may be provided with similar or different colors or surface indicia to impart varying aesthetic appearances. Further, a variation in color or surface indicia between one or more of the base, the cover, and the regulating plate may assist the user in properly aligning, securing, and/or operating various portions of the dispensers shown herein.

It is also contemplated that the various covers and bases described herein may have varying shapes and sizes. For example, the dispenser may be provided with a square cross-section, a circular cross-section, a hexagonal cross-section, or any other geometric cross-section. It is preferred that the base and the cover have a symmetrical shape such that the cover can be attached to the base regardless of its orientation. Further, it is preferable to include a plurality of covers that may be interchanged and provided with one or more bases to provide users the ability to choose a desired cover that is both functionally and aesthetically pleasing.

All documents cited in the Detailed Description of the Invention are, in relevant part, incorporated herein by reference; the citation of any document is not to be construed as an admission that it is prior art with respect to the present invention.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:
1. A dispenser, comprising:
    a base adapted to receive a volatile material containing reservoir therein;
    a cover attached to the base having an opening and at least one aperture and at least one series of ports; and
    a regulating plate operatively attached to the cover and having at least one window and a plurality of series of bores,
    wherein manipulation of a first series of bores of the regulating plate through the opening in the cover allows for the registration of at least a second series of bores and the at least one series of ports to release a volatile material therethrough.
2. The dispenser of claim 1, wherein the plurality of series of bores is disposed on a peripheral region of the regulating plate and the at least one window is disposed on a central region of the regulating plate.
3. The dispenser of claim 1, wherein at least the second series of bores is aligned along an edge of the at least one window on the regulating plate.
4. The dispenser of claim 1, wherein the plurality of series of bores is offset from an edge of the at least one window on the regulating plate.
5. The dispenser of claim 1, wherein the at least one window is configured to be registered with one or more of a plurality of apertures on the cover.
6. The dispenser of claim 1, wherein the at least one series of ports is disposed about a peripheral region of the cover.
7. The dispenser of claim 1, wherein the plurality of series of bores are equidistantly spaced about a peripheral region of the regulating plate.
8. The dispenser of claim 7, wherein each of the plurality of series of bores contains an equal number of bores.
9. The dispenser of claim 1, wherein the at least one window has a different geometric shape than the plurality of series of bores.

10. The dispenser of claim 9, wherein the at least one series of ports have the same geometric shape as the plurality of at least one series of bores.

11. The dispenser of claim 10, wherein the at least one aperture has the same geometric shape as the plurality of series of bores and the at least one series of ports.

12. The dispenser of claim 10, where the plurality of series of bores and the at least one series of ports are circular in shape.

13. The dispenser of claim 1, wherein the regulating plate includes three windows and three series of bores defining a peripheral ring about the three windows.

14. The dispenser of claim 13, wherein a plurality of apertures are provided for registration with the three windows.

15. A dispenser, comprising:
 a base adapted to receive a volatile material containing reservoir therein;
 a cover attached to the base having an opening and at least one aperture; and
 a regulating plate operatively attached to the cover and having at least one window and a series of bores,
 wherein the series of bores includes at least two bores, each of which is provided within a separate groove of the regulating plate, and
 wherein manipulation of one or more of the grooves of the regulating plate through the opening in the cover allows for the registration of one or more of the bores within the opening of the cover to provide a visual indication of a level of dispensing intensity.

16. The dispenser of claim 15, wherein at least one additional series of bores are provided within the regulating plate, which are adapted to be registered with a series of ports provided within the cover.

17. The dispenser of claim 16, wherein the series of bores are provided about a peripheral region of the regulating plate.

18. The dispenser of claim 16, further comprising three windows disposed within the regulating plate for registration with a plurality of apertures.

19. A dispenser, comprising:
 a volatile material containing reservoir;
 a cover having an opening and at least one aperture and a series of ports; and
 a regulating plate rotatably attached to the cover and having at least one window and a series of bores,
 wherein manipulation of at least a first bore of the regulating plate through the opening in the cover allows for the registration of at least a second bore and at least one of the ports spaced away from the opening, and at least partial alignment of the at least one aperture and the at least one window, wherein the series of ports and bores have a different geometric shape than the at least one window.

20. The dispenser of claim 19, wherein the degree of registration of the ports and the bores is proportional to the alignment of the at least one aperture and at least one window to release a volatile material therethrough.

\* \* \* \* \*